United States Patent [19]

Christianson

[11] Patent Number: 5,122,253

[45] Date of Patent: Jun. 16, 1992

[54] TRANSVERSE FORCED GAS COOLING FOR CAPILLARY ZONE ELECTROPHORESIS

[75] Inventor: John A. Christianson, Mountain View, Calif.

[73] Assignee: Hewlett-Packard Company, Palo Alto, Calif.

[21] Appl. No.: 522,279

[22] Filed: May 11, 1990

[51] Int. Cl.$^5$ ............... G01N 27/26; B01D 57/02
[52] U.S. Cl. ............... 204/299 R; 204/180.1
[58] Field of Search ............... 204/299 R, 180.1

[56] References Cited

U.S. PATENT DOCUMENTS

| | | | |
|---|---|---|---|
| 4,612,106 | 9/1986 | Kromer et al. | 204/299 R |
| 4,705,616 | 11/1987 | Andresen et al. | 204/299 R |
| 4,708,782 | 11/1987 | Andresen et al. | 204/299 R |
| 4,842,701 | 6/1989 | Smith et al. | 204/180.1 |
| 5,037,523 | 8/1991 | Weinberger et al. | 204/299 R |

*Primary Examiner*—John Niebling
*Assistant Examiner*—John S. Starsiak, Jr.

[57] ABSTRACT

An apparatus for capillary zone electrophoresis having a selectively removable capillary cassette, the internal walls of which define a toroidal capillary region and a gas flow path therethrough. Within the capillary region is housed a helically wound capillary tube having an inlet end and an outlet end. An electrical field is applied across the ends of the tube to cause electrophoretic separation of molecules of a sample. A stream of pressurized gas, preferably air, is channeled through the capillary region for cooling of the tube. The gas flow is a transverse flow and is channeled to avoid differentiation in cooling capacity. The transverse cross-sectional area of the gas flow path is substantially uniform throughout to prevent change in flow velocity. The gas flow path is a generally U-shaped path having a smooth radius turn. In progressing through the capillary region, the stream of gas is caused to flow at an angle relative to the axis of the helix, thereby promoting thermal isolation of succeeding loops of the helically wound capillary tube.

15 Claims, 3 Drawing Sheets

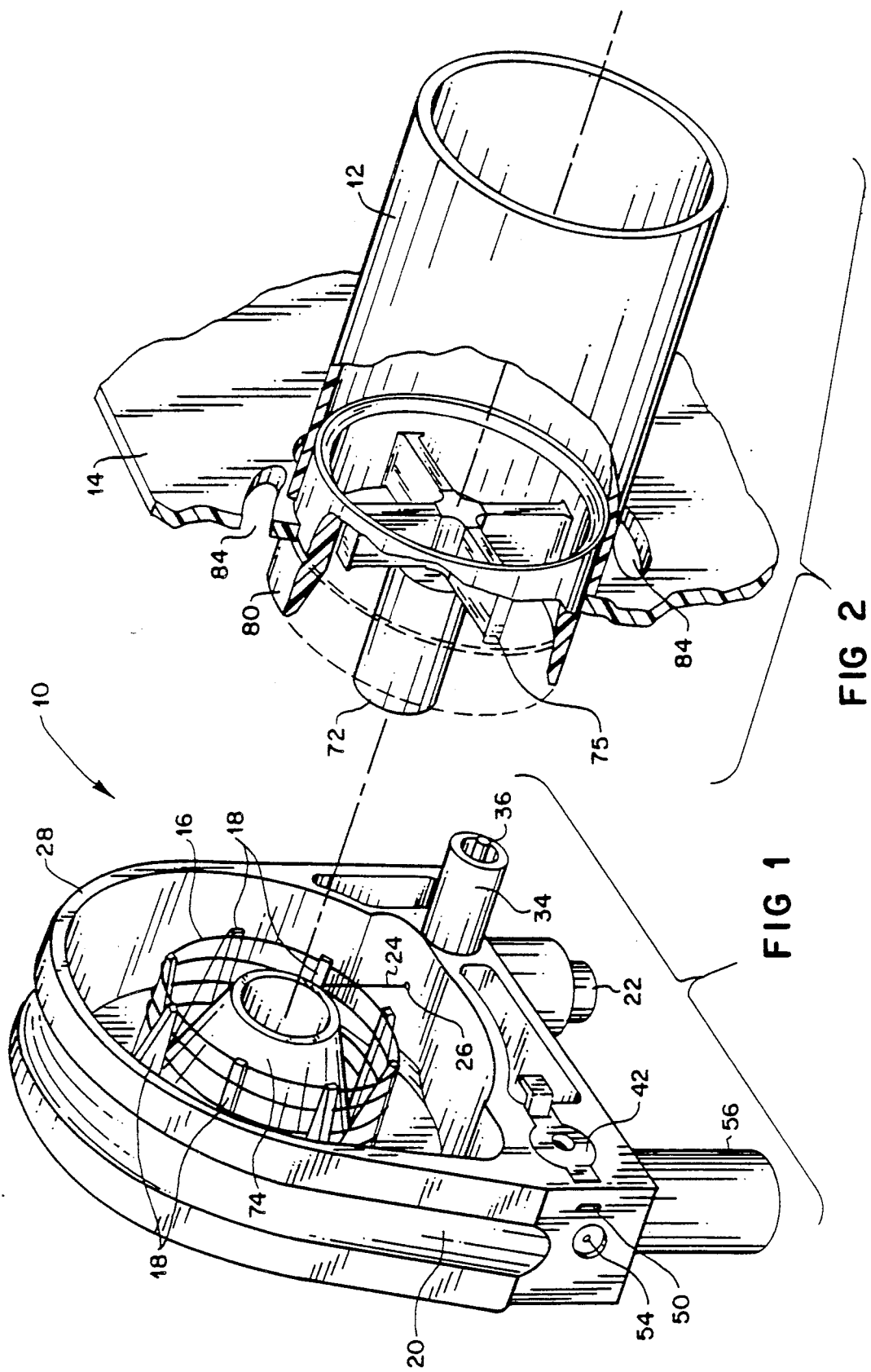

TRANSVERSE FORCED GAS COOLING FOR CAPILLARY ZONE ELECTROPHORESIS

TECHNICAL FIELD

The present invention relates generally to electrophoresis processes and particularly to cooling of an electrophoresis capillary tube.

BACKGROUND ART

Electrophoresis, as used in the fields of biology, molecular biology, biochemistry, clinical chemistry and medicine, is an analytical technique for separating and identifying biologically important molecules in a sample. Applications include the determination of a sample's homogeneality, the determination of molecular weights of proteins and nucleic acids, the mapping of nucleic acid primary structures, i.e. DNA and RNA sequence analyses, and the definition of phenotypic variance of a protein at the molecular level. A variety of techniques have been developed in order to accomplish these tasks. However, all these techniques rely on the fact that each molecular species has a unique combination of size, shape, charge, density, and sub-unit structure. Each of the electrophoretic techniques uses one or more of these parameters to cause varying degrees of molecular separation via the migration of the molecular species under the influence of an electric field.

One technique for separation of molecules is referred to as capillary zone electrophoresis. This technique uses a capillary tube which is filled with a conductive fluid, or buffer solution. A small amount of a sample is introduced at one end of the capillary tube, whereafter a high potential difference is applied across the ends of the tube. Differences in the electrophoretic mobilities of different molecules cause the constituents of the sample to emerge separated at the outlet end of the capillary tube. Capillary zone electrophoresis is described in greater detail in U.S. Pat. No. 4,842,701 to Smith et al.

One concern in electrophoresis separation by use of an electromotive force is maintaining the temperature of the capillary tube within a desired range. A typical potential difference across the ends of the capillary tube is in the range of 20,000 to 30,000 volts. Current through the capillary tube causes heating of the solution and the capillary tube. Heating affects, and may completely destroy, results of the quantitative and qualitative analysis. The biological sample within the buffer solution may be damaged or destroyed by excessive heat. Moreover, boiling may occur and cause a recurring loss of electrical conduction, and therefore, produce a lower or diminished current flow and a breakdown of the electrophoresis process.

One method of controlling the temperature of electrophoresis process is to use a heat sink for the capillary tube. U.S. Pat. No. 4,708,782 to Andresen et al. teaches use of a heat sink for the capillary. Likewise, U.S. Pat. No. 4,705,616 to Andresen et al. teaches the heat sink and further provides a double-feed-line approach which allows the capillary electrophoresis probe tip to be continually wetted by the buffer so as to improve heat dissipation. U.S. Pat. No. 4,612,106 to Kromer et al. is related to gel slab electrophoresis, but that patent also teaches use of a heat sink as being critical to temperature control. A serpentine piping through the heat sink provides an air circulating system to augment heat dissipation.

Cooling methods other than use of a heat sink are known. In each case, it is important to address the problem of isolating the high voltage source associated with capillary zone electrophoresis. As noted above, a potential difference of 30,000 volts may be employed. Immersing the capillary tube in tap water to dissipate the heat is risky because tap water is conductive and, if the capillary tube were to form a crack or if the electrodes were not well isolated from the water, unsafe charging of the ungrounded water or shorting to grounded water could occur. De-ionized water may be a better choice, but any contamination may render the water conductive. A known solution is to use a cooled oily, non-conductive, perfluorinated fluid with a high dielectric strength to contact the capillary tube. The use of the specialized oily fluid, unfortunately, is expensive and sometimes cost-prohibitive. Moreover, the oily fluid causes difficulties in cleanup after completion of the electrophoresis process. Another method may be to achieve a degree of capillary zone electrophoresis cooling by use of air in contact with the capillary tube. The drawbacks are that still air does not sufficiently conduct heat away from the capillary tube, and that a flow of air along the length of the capillary tube creates temperature differentiation within the tube as the air is heated by continued flow along the length.

An object of the present invention is to provide an apparatus for electrophoretic separation using a capillary tube, wherein temperature control is provided in a manner which isolates heat dissipation to achieve a uniform cooling and which isolates the operational high voltage source.

DISCLOSURE OF THE INVENTION

The above object has been met by an electrophoretic apparatus which uses a cooling medium that is electrically non-conductive and readily available to thermally control a capillary tube by conducting heat away from localized regions of the capillary tube. That is, a non-conducting gas, preferably air, is used as a cooling medium and is channeled in a manner which promotes uniform cooling throughout the capillary tube. The electrophoresis process is affected by the heat of the process, so that maintaining an approximately uniform temperature throughout the capillary tube increases the reliability of a quantitative and qualitative analysis of a sample.

The present invention utilizes a flow of pressurized gas to cool a capillary tube. The pressurized gas flow negates the necessity of use of a heat sink that is taught by the patents of Andresen et al. and Kromer et al., cited above. One concern with the use of heat sinks is the choice of materials. Electrically non-conductive materials are preferred for the purpose of isolating the high voltage. However, materials which are characterized by poor electrical conductivity are typically also characterized by poor thermal conductivity. A second concern is formation of condensation on the heat sink, since condensation normally occurs at the coolest region of the system. Condensation affects the uniformity of cooling, and in any case is not desirable.

The present invention includes a housing having a capillary region and a gas flow path therethrough. An electrophoresis capillary tube is mounted within the capillary region and is preferably coiled into a helical configuration. A stream of pressurized gas flows through the capillary region to dissipate the heat caused by the electrical current through the capillary tube.

Features which promote uniform cooling include channeling the gas so that the major directional component of the gas flow through the capillary region is perpendicular to the tube. In contrast to a longitudinal flow along the capillary tube, this transverse flow isolates regional heat dissipation. In longitudinal flow or in the serpentine flow taught by the patent to Kromer et al., the stream of gas is heated as the stream progresses along the object to be cooled. This heating causes thermal differentiation along the object to be cooled.

Other features which promote uniform cooling of the capillary tube include causing the gas stream to progress at an acute angle to the axis of the helically wound capillary tube. This angular flow is preferred to a flow which progresses parallel to the axis of the helix because the parallel flow meets each succeeding loop of the helix with gas molecules which were heated by contact with preceding loops. Other features include providing a substantially constant cross sectional area of the gas flow paths so that the flow velocity remains constant. It has been discovered that a constant velocity within the range of 5 m/s to 10 m/s is optimal. Yet another feature which promotes uniformity of cooling is the configuration of the gas flow path. The flow path is U-shaped and has a smooth turn. By reducing the turns to a minimum and by providing smooth radius turns significant pressure drops are avoided and a less powerful source of pressurized gas is necessary.

In addition to thermal uniformity throughout the capillary tube, an advantage of the present invention is that the cooling medium is inexpensive and is clearly cleaner than the oily, non-conductive, perfluorinated fluid used in some applications.

BRIEF DESCRIPTION OF THE DRAWINGS

FIG. 1 is a perspective view of a capillary cassette for supporting a capillary tube in accord with the present invention.

FIG. 2 is perspective view of a support structure for the capillary cassette of FIG. 1.

BEST MODE FOR CARRYING OUT THE INVENTION

Figure 3:
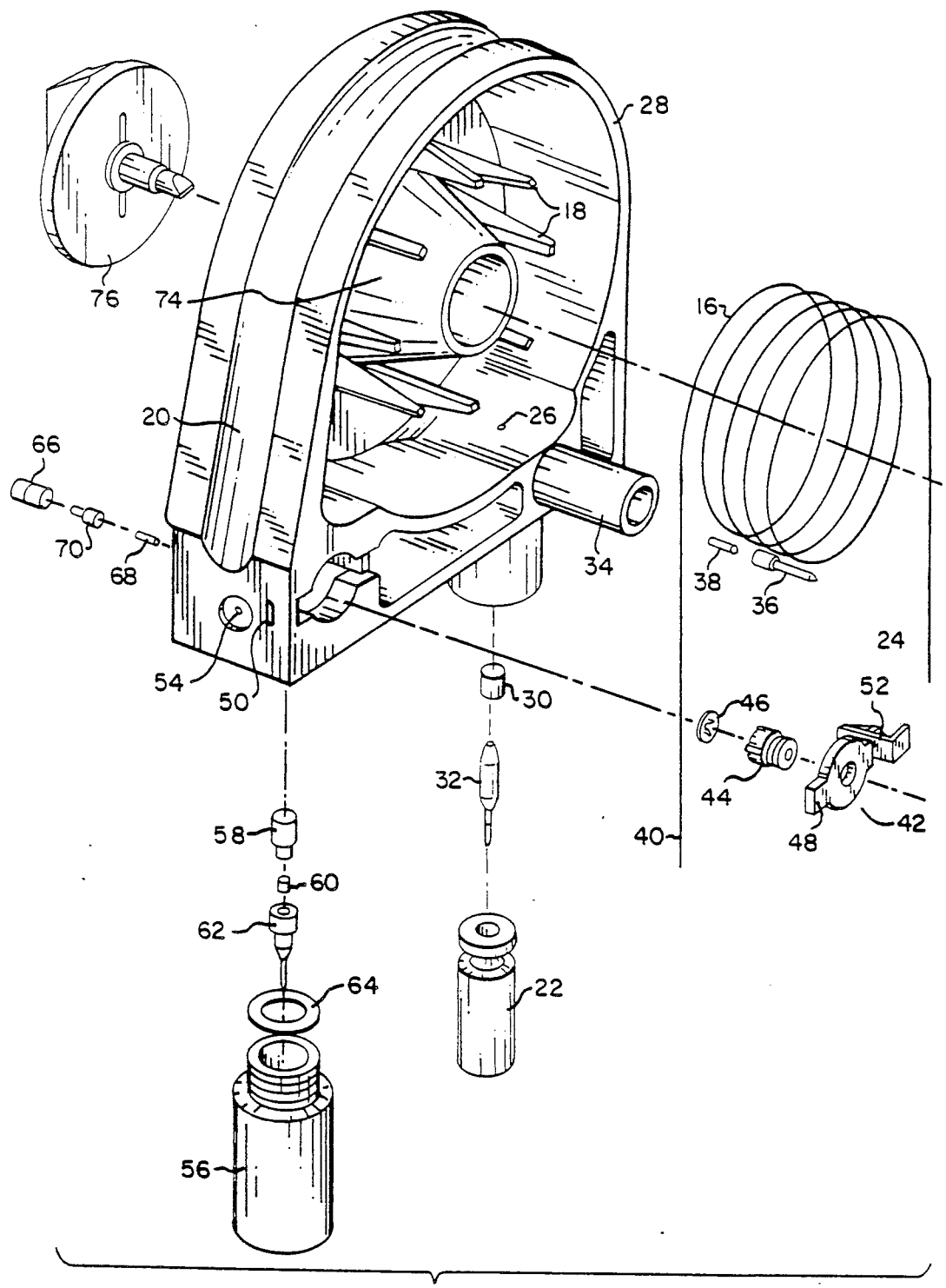
FIG. 3 is an exploded view of the capillary cassette of FIG. 1.

With reference to FIGS. 1 and 2, a capillary cassette 10 is shown in alignment for attachment to a fixed support structure which includes a cylindrical fan housing 12 and a front support wall 14. A capillary tube 16 is maintained in a coiled condition by a capillary basket that includes a series of ribs 18 that alternate in orientation. The capillary cassette 10 is removably attached to the front support wall 14. A groove 20 about the exterior of the capillary cassette facilitates gripping of the member during removal.

In capillary zone electrophoresis, separation of molecules occurs within the capillary tube 16. Referring to FIGS. 1 and 3, a sample vial 22 is attached at an inlet end 24 of the capillary tube 16. The inlet end 24 is inserted into a small diameter bore 26 in a cassette shell 28, then passes through an anode insert 30 for attachment to an anode electrode 32. The capillary tube 16 is filled with a conductive fluid, or buffer, after which a small amount of the sample to be separated is introduced at the inlet end 24 either hydrodynamically or electroosmotically. A d.c. potential of up to 30,000 volts is applied at the anode electrode 32 to provide an electromotive force for separation of molecules. The separation is a result of differences in electrophoretic mobility of the molecules.

A protective sleeve 34 projecting from the cassette shell 28 encases an anode contact 36 and a helical spring 38. The helical spring is metallic and is included to ensure electrical communication between the anode contact 36 and the anode insert 30. Upon mounting of the capillary cassette 10 onto the support structure identified above, the protective sleeve 34 is slidably received within the support wall of the structure and the anode contact 36 is caused to make contact with a source of power.

The construction of the capillary tube 16 is known in the art. Preferably, for the present invention the capillary tube is made of fused-silica. A fused-silica tube may be trained into the illustrated helical condition by the ribs 18 of the capillary basket, but such a tube is characterized by a memory which urges return of the capillary tube into a generally straight condition. Typically, the capillary tube has an inside diameter of 50 micron and outside diameter of 375 micron. The ribs 18 of the capillary basket accommodate 20 cm to 1 meter long fused-silica capillary tubes. Often the fused-silica is encased within a coating of polyimide.

The polyimide coated, fused-silica capillary tube 16 is cut to a desired length and the inlet end 24 of the capillary tube is brought into fluid communication with the sample vial 22 and into electrical communication with a source of high voltage via the anode contact 36. Approximately 3 cm from an outlet end 40 of the capillary tube 16 a window is formed through the polyimide coating. The outlet end 40 is inserted into the capillary shell 28 and the window is aligned along an optical path provided by an aperture clip 42, an aperture mount having a helical spring 44 and an optical aperture member 46. The combination of the aperture mount and the optical aperture member secures the capillary tube in the desired position. The aperture clip 42 is a snap-in member which allows a user to quickly align and clamp the capillary tube without the use of tools. A projecting end 48 of the aperture clip 42 is received within a seat 50 in the cassette shell 28. The opposite end 52 of the aperture clip is selectively released from the cassette shell by a slight bending action of the member. Each of the members 42, 44 and 46 which seat the outlet end 40 of the capillary tube allow passage of optical detection such as by an ultraviolet absorbance detector.

Adjacent to the seat 50 of the cassette shell 28 which receives the projecting end 48 of the aperture clip 42, is a vacuum port 54 which is used in drawing a sample from the sample vial 22. The outlet end 40 of the capillary tube 16 is in fluid communication with a reservoir vial 56. To properly mount the outlet end with the reservoir vial, the capillary tube progresses through a cathode insert 58, a deformable ferrule 60, a cathode electrode 62 and a vacuum seal 64. The cathode electrode 62 is an electrical communication with a cathode connector 66 that is received within a bore, not shown, in the front of the cassette shell 28. A cathode spring 68 biases a plunger 70 and the cathode connector 66 into contact with a member at ground potential relative to the positive potential at the inlet end 24 of the capillary tube.

Referring now to FIGS. 1-3, in attaching the capillary cassette 10 to the support structure which includes the cylindrical fan housing 12 in the front support wall 14, a seating rod 72 of the support structure is received within a frustroconically shaped wall 74 of the capillary cassette. Four radial arms 75 secure the seating rod 72. A locking knob 76, shown in FIG. 3, is inserted into the seating rod of the support structure, whereafter a 90° turn of the locking knob causes fastening of the capillary cassette 10 to the support structure. In connecting the capillary cassette to the support structure, the window in the capillary tube is aligned for optical viewing by an ultraviolet absorbance detector, the anode contact 36 is brought into electrical connection with a power source, and the capillary tube is positioned to receive a cooling flow of pressurized air generated by a rotary fan 78 shown in FIG. 4.

Figure 4:
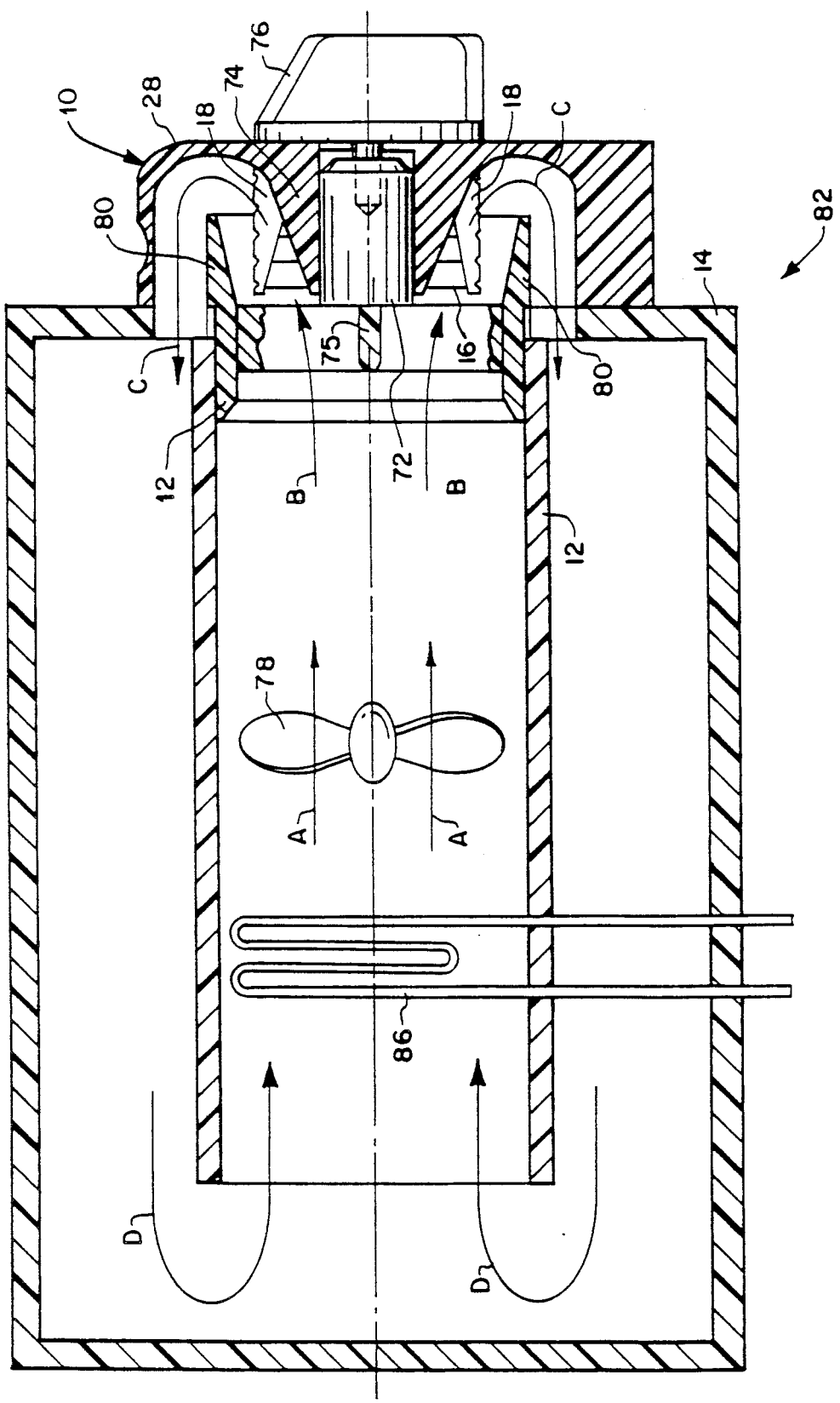
FIG. 4 is a side sectional view of the capillary cassette of FIG. 1 attached to the support structure of FIG. 2.

Referring to FIGS. 2 and 4, the rotary fan 78 creates a gas flow which is axial to the helix formed by the capillary tube 16, as shown by arrows A. As the gas flow enters a capillary region between the frustroconically shaped wall 74 of the capillary cassette 10 and a projection wall 80 of the support structure, the frustroconically shaped wall 74 acts as a deflection surface to provide angular flow of the stream of gas relative to the axis of the helix.

The gas stream through the capillary region between the frustroconically shaped wall 74 and the projection wall 80 is a transverse flow relative to the capillary tube 16. That is, the major directional component of the gas flow through the capillary region is perpendicular to the molecular flow through the capillary tube. It has been discovered that in the embodiment shown in FIG. 4, a gas flow velocity in the range of 5 m/s and 10 m/s is optimal. Utilizing a capillary tube having an inside diameter of 50 micron and an outside diameter of 375 micron at a power dissipation of 0.64 W/cm$^2$ and a flow rate 5 m/s, the difference in temperature between the inside diameter and the outside diameter of the capillary tube is less than 20° C. At 10 m/s the temperature difference drops to less than 15° C. Because the flow is a transverse flow through the capillary region, rather than a longitudinal flow along a linear capillary tube, thermal dissipation from a localized region of the tube is isolated. That is, thermal dissipation from the localized region does not heat the gas flow that must cool a succession of localized regions. Instead, gas molecules which are heated by contact with a first loop of the helically wound capillary tube are forced outwardly by the deflection surface of the frustroconically shaped wall 74 so as not to come in contact with succeeding loops. Thus, uniformity of capillary tube cooling is promoted.

The capillary region between the walls 74 and 80 has a toroidal shape. The inside surface of the projection wall 80 has an incline which is less than the incline of the frustroconically shaped wall 74. The difference in the slopes of the walls 74 and 80 is such that the cross-sectional area through the capillary region remains uniform. Uniformity of area is important since an increase or decrease in area will inversely affect the velocity of the gas through the capillary region. On the other hand, a constant flow velocity aids in maintaining consistent cooling throughout the capillary region. As noted above, temperature affects the electrophoretic process. Therefore, uniformity of temperature along the entirety of the capillary tube influences the reliability of the quantitative and qualitative analysis. In the embodiment of FIG. 4, the slope of the frustroconically shaped wall 74 is approximately 21.5° to the axis of the helix, while the projection wall 80 is at an angle of 12°.

Arrows B in FIG. 4 illustrate the flow of gas which is deflected by the wall 74 upon entering the capillary region. The internal wall of the capillary cassette provides a U-shaped flow path, as shown by arrows C. The flow path remains constant in cross-sectional area until exiting the front support wall 14 of the support structure 82. By maintaining the uniform cross-sectional area, by providing a smooth radius turn, and by reducing the flow to a single turn, the present invention provides a constant cooling process throughout the capillary region. That is, these three features along with the transverse flow promote uniform cooling of the capillary tube 16.

As shown in FIG. 2, the front support wall 14 of the support structure includes a number of crescent shaped openings 84 which permit return flow of the gas from the capillary cassette 10. Returning to FIG. 4, the flow of gas then returns to the cylindrical fan housing 12, as shown by arrows D. The temperature of the gas within the apparatus is controlled by contact with a heat exchanger 86 having a coolant flow therethrough.

In operation, the capillary tube 16 is releasably mounted within the capillary cassette 10 of FIGS. 1 and 3. Vacuum injection of a sample into a buffer fluid is followed by application of a high voltage across the inlet end 24 and outlet end 40 of the capillary tube. Sample molecules having differing electrophoretic mobility are separated and then detected at the outlet end for a quantitative and qualitative analysis.

The capillary tube 16 is cooled by a flow of gas which is a transverse flow. Preferably air is used as the cooling medium, but other gases such as dry nitrogen may be employed in the closed system to avoid shorting problems due to condensation formation at temperatures below the dew point. In addition to being a transverse flow within the capillary region, the stream of gas flows at an angle relative to the axis of the capillary tube. Consequently, heat dissipation from one localized region of the capillary tube is not carried along other regions of the capillary tube. Thermal isolation is achieved by such a flow. Moreover, the flow path through the cassette is designed so that the flow remains at a constant velocity to prevent differentiation in cooling capacity. The constant velocity is achieved by maintaining a uniform cross-sectional area through the flow path with a single, smooth radius turn.

I claim:

1. An apparatus for electrophoretic separation comprising,
    a housing having a capillary region and a gas flow path through said capillary region, said gas flow path having a generally U-shaped cross section, said U-shape defined by said housing,
    an electrophoresis capillary tube supported within said capillary region of said housing, said capillary tube defining a molecular flow path having an inlet end and an outlet end,
    cooling means for creating a pressurized gas flow along said gas flow path, said capillary tube positioned such that the major directional component of said gas flow through said capillary region is perpendicular to said molecular flow path, and
    means for connecting an electrical potential difference across said inlet end and said outlet end of the capillary tube, thereby connecting an electrical potential difference sufficient to cause electrophoretic migration within said capillary tube.

2. The apparatus of claim 1 wherein the gas flow path has substantially uniform transverse cross-sectional area through said capillary region, thereby providing a generally constant velocity of gas flow through said capillary region.

3. The apparatus of claim 1 wherein said capillary tube has a helical configuration, said gas flow entering said capillary region from a direction coinciding with the axis of said helical configuration.

4. The apparatus of claim 3 wherein said capillary region has a toroidal configuration to receive said helical capillary tube, said toroidal capillary region having an arcuate gas flow deflection surface adapted to cause a gas flow which is at an angle relative to the axis of said helical capillary tube.

5. The apparatus of claim 4 wherein said deflection surface has a U-shaped transverse cross section and wherein said housing includes a wall extending into said U-shape, said wall being spaced apart from said deflection surface to permit gas flow about said wall, said gas flow path having an inlet on a first side of said wall and an outlet on a second side.

6. The apparatus of claim 1 further comprising heat exchange means for regulating the temperature of said gas flow.

7. The apparatus of claim 6 wherein said cooling means directs said ga flow through said capillary region at a velocity in the range of 5 m/s to 10 m/s.

8. An apparatus for electrophoretic separation comprising,
   a housing having walls defining a capillary region and a gas flow path through said capillary region, said capillary region having a toroidal configuration,
   mounting means for supporting a helically wound capillary tube in said capillary region in a manner which suspends at least one portion of said capillary tube,
   an electrophoresis capillary tube helically supported within said capillary region by said mounting means, said capillary tube having at least one suspended portion exposed to the ambient atmosphere of said capillary region, said capillary tube having an inlet end and an outlet end,
   pressurized gas flow means for directing a cooling gas through said capillary region substantially along the axis of said helically supported capillary tube and in direct heat-transfer contact with said exposed portion of said capillary tube, said flow means directing gas flow past an exposed portion in a direction substantially perpendicular to the length of said exposed portion, said capillary region of said housing partially defined by a gas flow deflection surface which is at an acute angle relative to said axis of said helically supported capillary tube, and
   means for connecting a high electrical potential across said capillary tube to cause electrophoretic separation within said capillary tube.

9. The apparatus of claim 8 wherein said deflection surface has a U-shaped cross section and wherein said housing includes a wall extending into said U-shape, said wall being spaced apart from said deflection surface to permit gas flow thereabout, said gas flow path having an inlet on a first side of said wall and an outlet on a second side.

10. The apparatus of claim 9 wherein said gas flow path has a substantially uniform cross-sectional area from said inlet to said outlet, thereby maintaining a generally uniform velocity of flow.

11. The apparatus of claim 10 wherein said flow velocity is in the range of 5 m/s to 10 m/s.

12. An apparatus for electrophoretic separation comprising,
    an electrophoresis capillary tube having an inlet end and an outlet end,
    a housing having a gas flow path, said gas flow path having a substantially uniform cross-sectional area therethrough, said housing having walls to define said gas flow path, said walls having a toroidal shape having an inclined wall at an inside diameter,
    mounting means for supporting said capillary tube within said gas flow path of the housing, said mounting means being adapted to maintain said capillary tube in a helical configuration,
    cooling means for channeling a stream of pressurized gas through said gas flow path, said stream of gas being directed generally axially toward said helical capillary tube and in contact with said capillary tube, and
    means for connecting a high voltage between said inlet and outlet ends of said capillary tube.

13. The apparatus of claim 12 wherein said stream of gas has a velocity in the range of 5 m/s to 10 m/s upon progressing through said capillary region.

14. The apparatus of claim 12 wherein said gas flow path has a generally U-shaped cross section having a smooth turn.

15. The apparatus of claim 12 further comprising heat exchange means for controlling the temperature of said stream of pressurized gas.

* * * * *